(12) United States Patent
Kocsis et al.

(10) Patent No.: US 12,419,756 B2
(45) Date of Patent: Sep. 23, 2025

(54) GLENOID PROSTHESIS BASEPLATE

(71) Applicants: SEMMELWEIS EGYETEM, Budapest (HU); BUDAPESTI MŰSZAKI ÉS GAZDASÁGTUDOMÁNYI EGYETEM, Budapest (HU)

(72) Inventors: György Kocsis, Budapest (HU); Gábor Szebényi, Vecsés (HU)

( * ) Notice: Subject to any disclaimer, the term of this patent is extended or adjusted under 35 U.S.C. 154(b) by 0 days.

(21) Appl. No.: 18/729,690

(22) PCT Filed: Jan. 9, 2023

(86) PCT No.: PCT/HU2023/050001
§ 371 (c)(1),
(2) Date: Jul. 17, 2024

(87) PCT Pub. No.: WO2023/135436
PCT Pub. Date: Jul. 20, 2023

(65) Prior Publication Data
US 2025/0099254 A1 Mar. 27, 2025

(30) Foreign Application Priority Data

Jan. 17, 2022 (HU) .................................. P2200014

(51) Int. Cl.
*A61F 2/40* (2006.01)
*A61F 2/30* (2006.01)
*A61F 2/46* (2006.01)

(52) U.S. Cl.
CPC .... *A61F 2/4081* (2013.01); *A61F 2002/3006* (2013.01); *A61F 2002/30331* (2013.01); *A61F 2002/30387* (2013.01); *A61F 2002/305* (2013.01); *A61F 2002/30578* (2013.01); *A61F 2/30767* (2013.01); *A61F 2002/30784* (2013.01); *A61F 2002/30787* (2013.01); *A61F 2002/3093* (2013.01); *A61F 2002/4085* (2013.01); *A61F 2/4612* (2013.01);
(Continued)

(58) Field of Classification Search
CPC ...... A61F 2/30767; A61F 2/4081; A61F 2/40; A61F 2/4612; A61F 2002/3006; A61F 2002/30331; A61F 2002/305; A61F 2002/30387; A61F 2002/30607; A61F 2002/4085; A61F 2002/30578; A61F 2002/30784; A61F 2002/30787; A61F 2002/3093; A61F 2250/0062; A61F 2220/0041; A61F 2220/0033; A61F 2220/0025; A61B 17/1684; A61B 17/1778; A61B 17/80
USPC ....... 606/53, 280, 281, 86 R, 86 B, 902, 915
See application file for complete search history.

(56) References Cited

U.S. PATENT DOCUMENTS

| 2007/0100458 A1* | 5/2007 | Dalla Pria | A61F 2/4081 623/19.13 |
| 2018/0103967 A1* | 4/2018 | Rouyer | A61B 17/1659 |

* cited by examiner

Primary Examiner — Marcela I. Shirsat

(57) ABSTRACT

The invention discloses a glenoid prosthesis baseplate, having a surface (1) for an artificial socket insert, an opposite fitting surface (2), and holes (2f) passing through the surfaces (1, 2), and feet (3) on the surface (1) for the artificial socket insert for fixing the artificial socket insert. The baseplate has at least two mounting tabs (4) connected to the edge (P) of the baseplate, and holes (4a) passing through each mounting tab (4), and the prosthesis baseplate is provided with at least two through holes (2f) passing through both the surface (1) for the artificial socket insert and the fitting surface (2), and each hole (2f) being in alignment with the axis of a through hole (4a) of the mounting tab (4).

5 Claims, 2 Drawing Sheets

Figure 2:
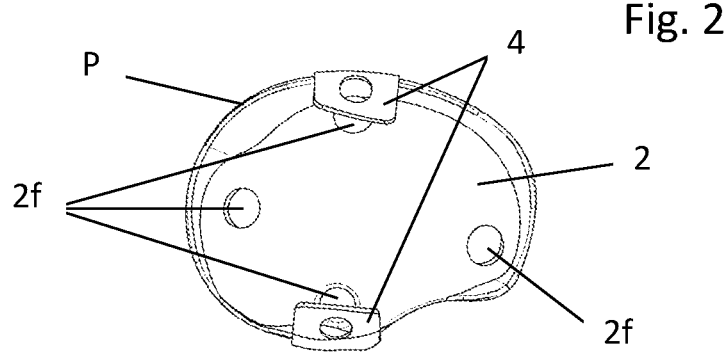

(52) U.S. Cl.
CPC ................ *A61F 2220/0025* (2013.01); *A61F 2220/0033* (2013.01)

GLENOID PROSTHESIS BASEPLATE

The invention relates to a glenoid prosthesis baseplate, having a surface for an artificial socket insert, an opposite fitting surface, and holes passing through the surfaces, and feet on the surface for the artificial socket insert for fixing the artificial socket insert.

During the creation of complete shoulder prostheses, both the articular head of the humerus and the socket of the scapula are replaced by implanting prosthetic components. The prosthesis of the socket of the scapula is placed on the glenoid, the part of the scapula that originally functions as a socket. The glenoid component of the prosthetic system is made entirely of polyethylene, or of a metal baseplate attached to the scapula bone and a polyethylene insert arranged on the opposite side of the metal baseplate. In the case of using a metal baseplate, the side of the baseplate facing the bone has a surface treatment that promotes bone ingrowth, and it is equipped with at least one fixing pin, a so-called peg, which sinks into the bony stock of the glenoid. On the one hand, the peg increases the surface suitable for bone ingrowth, on the other hand it absorbs the transverse forces that arise in the plane of the baseplate, and also plays a role in neutralizing the eccentric pressing forces transmitted by the head of the humerus. The more robust the peg is, the more effectively it neutralizes the mentioned forces, which is why known glenoid baseplates use increasingly larger and mostly centrally located pegs.

However, the large peg sunk into the glenoid bone material transmits the applied physiological load to the deeper parts of the glenoid, that is to the neck of the scapula. Since bone is a dynamic tissue, its areas without physiological load can degrade and thus weaken over time. Considering that forces up to one and a half times the body weight can be generated on a few square centimetres of the socket of glenoid, the weakening of the bone can lead to a fracture even under normal loads.

Therefore, the U.S. Pat. No. 1,0702,390 describes a glenoid baseplate prosthesis that has a first surface in contact with the glenoid surface of the scapula, a second surface that accommodates the head of the humerus, and a cylindrical anchor pin that protrudes from the first surface and it is sunk into the glenoid surface of the scapula, on which elastic ribs are placed that stretch into the anchor hole formed in the scapula. Thus, the anchor pin, i.e., the peg, is not directly in contact with the inner surface of the hole made for the peg in the glenoid bone, but via the flexible ribs.

With this solution, it is possible to reduce the unweakened transmission of the forces absorbed by the peg into the deeper layers of the bone tissue, but in order to insert the large, deeply extending peg, a significant proportion of the bone mass of the already small glenoid must be removed, which on the one hand further reduces the strength of the scapula, and on the other hand, results in a shortage of bone mass for any possible subsequent restorative surgery, not to mention the fact that during the implantation of a large peg, the cortical material of the bone can be perforated which has been proven to contribute to the continuous loosening of the prosthesis.

Our objective with the invention is, therefore to create a glenoid socket prosthesis, with which, on the one hand, the transmission of the forces absorbed by the peg into the deeper layers of the bone tissue can be further reduced by a pegless construction, and at the same time, there is no need to remove a significant portion of the bone mass from the glenoid stock, and on the other hand, accidental perforation of the bone's cortical stock can be avoided.

We realized that if the central anchor pin, i.e., the peg, is partially or completely omitted and the baseplate of the socket prosthesis is fixed on the rim of the glenoid, then the disadvantages of the state-of-the-art solutions can be eliminated.

We therefore achieved our object by providing a glenoid prosthesis baseplate, having a surface for an artificial socket insert, an opposite fitting surface, and holes passing through the surfaces, and feet on the surface for the artificial socket insert for fixing the artificial socket insert, and at least two mounting tabs connected to the edge of the baseplate, and holes passing through each mounting tab, and the prosthesis baseplate is provided with at least two through holes passing through both the surface for the artificial socket insert and the fitting surface, and each hole being in alignment with the axis of a through hole of the mounting tab.

The surface for the artificial socket insert is preferably provided with a groove for fitting the insert.

The fitting surface is provided with a coating promoting bone ingrowth.

The fitting surface is provided with a polyethylene coating.

An internal thread is formed in the through hole.

Figure 6:
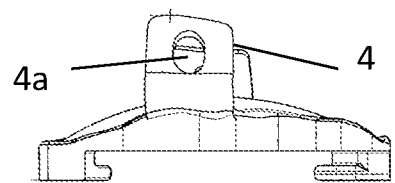
Figure 7:
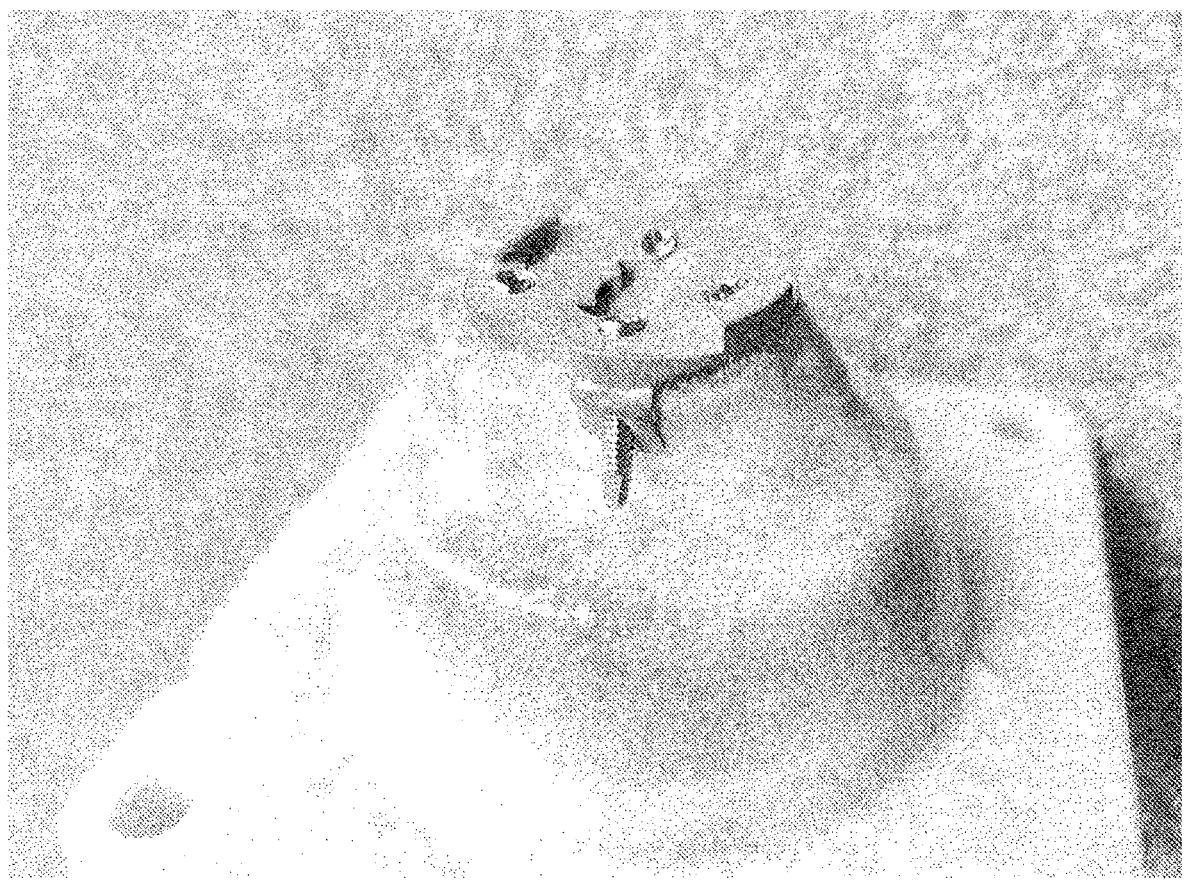

The invention will be described in detail below by reference to the attached drawing. In the drawing FIG. 1 is a side view of the glenoid prosthesis baseplate according to the invention, FIG. 2 shows the glenoid prosthesis baseplate according to the invention in a bottom view, FIG. 3 shows the glenoid prosthesis baseplate according to the invention in a top view, a FIG. 4 shows the glenoid prosthesis baseplate according to the invention in a front view, FIG. 5 shows the glenoid prosthesis baseplate according to the invention in a rear view, FIG. 6 is a further side view of the glenoid prosthesis baseplate according to the invention, and FIG. 7 is a photograph showing the position of the baseplate fixed with screws on an artificial glenoid surface.

Figure 1:
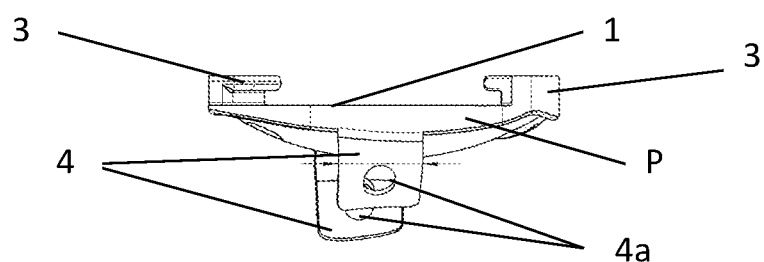

FIG. 1 shows a side view of the baseplate of the glenoid prosthesis baseplate according to the invention. The prosthesis baseplate has a surface 1 on the side of the artificial socket insert, not shown in the figure, and a fitting surface 2 opposite to it, where the fitting surface 2 is a surface 2 with a convex design well known to the person skilled in the art, that can be fitted into the concave socket of the glenoid. The artificial socket insert, not shown in the figure, which is usually made of polyethylene, can be slid into the fixing feet 3 for fixing the artificial socket insert arranged along the edges of the surface 1, and it can be fixed there. At least two mounting tabs 4 are arranged along the circumferential edge P of the fitting surface 2. At least two of the 4 mounting tabs face each other spaced apart, in the embodiment shown, at an angular distance of 180° along the circumferential edge P of the fitting surface 2 of the prosthesis baseplate. In the embodiment as shown, two mounting tabs 4 and four through holes 2f are used to fasten the baseplate, so that two holes 2f of the through holes 2f are co-axial with the through hole 4a of one of the mounting tabs 4 that is closer to it. Of course, several mounting tabs 4 and through holes 2f having the same axis in pairs can also be used.

Figure 3:
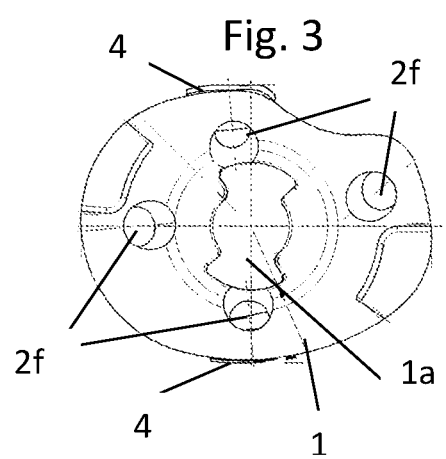

FIG. 2 shows a bottom view of the glenoid prosthesis baseplate the according to the invention. The through holes 2f formed on the fitting surface 2 of the baseplate penetrate the entire thickness of the baseplate and emerge on the surface 1, as it can be seen in FIG. 3 showing the baseplate in a top view. In FIG. 3, a central groove 1a is also visible in the middle of the surface 1, which serves to center, orient and fix the artificial socket, in addition to the fixing feet 3.

Figure 5:
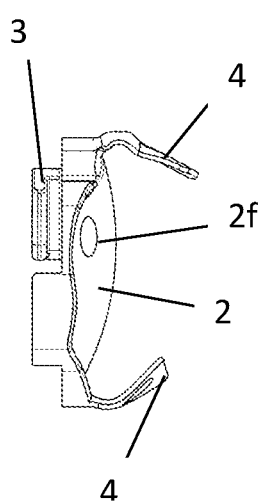
Figure 4:
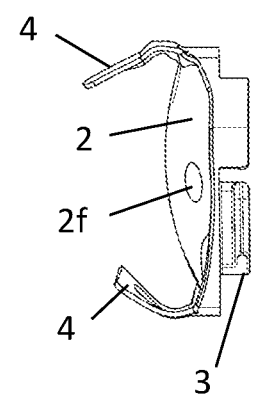

In FIGS. 4 and 5, which depict the baseplate in front and rear views, the mounting tabs 4 and the through holes 2f having no corresponding mounting tabs 4 can also be observed. With these 2f through holes the glenoid prosthesis baseplate can be fixed with blind holes deepened into the glenoid bone or mounting tabs 4 can be arranged for these holes 2f as well. In this case the through holes 2f are formed co-axially with the mounting tabs 4 indeed.

The task of the through holes 4a formed on the mounting tabs 4 shown in FIGS. 1 and 6 is to fix a connecting element e.g. a screw C inserted into the through holes 2f arranged near the mounting tabs 4 and provided with an internal thread in the holes 4a as well, as it is shown in FIG. 7 a photograph depicting the baseplate in a position as fixed on an artificial glenoid surface. In the embodiment shown two mounting tabs 4 and four through holes 2f are used to fix the baseplate so that two screws C driven into two through holes 2f of the through holes 2f also pass into and fit with their threads in through holes 4a to fix the baseplate to the surface of the glenoid. In a non-illustrated embodiment, a rivet or an endless fastening strap, if appropriate, can also be used instead of screw C. In this case it is not necessary to create an internal thread in the through holes 2f.

In summary, the glenoid prosthesis baseplate according to the invention has a surface 1 for an artificial socket insert, an opposite fitting surface 2, and holes 2f passing through the surfaces 1, 2, and feet 3 on the surface 1 for the artificial socket insert for fixing the artificial socket insert, and at least two mounting tabs 4 connected to the edge P of the baseplate and holes 4a passing through each mounting tab 4. The prosthesis baseplate is provided with at least two through holes 2f passing through both the surfaces 1 for the artificial socket insert and the fitting surface 2, and each hole 2f being in co-axial alignment with the axis of a through hole 4a of the mounting tab 4, that is having a common axis passing through the middle point of the respective holes 2f, 4a. The surface for the artificial socket insert is preferably provided with a groove for fitting the insert. The fitting surface 2 is provided with a coating promoting bone ingrowth. The fitting surface 2 is provided with a polyethylene coating. An internal thread is formed in the through hole 2f.

The advantage of the glenoid prosthesis baseplate according to the invention compared to the state-of-the-art solutions is that it is possible to further reduce the transmission of the forces absorbed by the previously used peg into the deeper layers of the bone tissue, and there is no need to remove a significant proportion of bone mass from the glenoid stock, and damage to the bone's cortex by accidental piercing can also be avoided.

The invention claimed is:

1. A glenoid prosthesis baseplate, comprising a surface (1) for an artificial socket insert, an opposite fitting surface (2), and holes (2f) passing through the surfaces (1,2), and feet (3) on the surface (1) for the artificial socket insert for fixing the artificial socket insert, two mounting tabs (4) connected to the edge (P) of the baseplate, and holes (4a) passing through each mounting tab (4), and the prosthesis baseplate provided with at least two through holes (2f) passing through both the surface (1) for the artificial socket insert and the fitting surface (2), and each hole (2f) being in alignment with the axis of a through hole (4a) of the mounting tab (4).

2. The glenoid prosthesis baseplate according to claim 1, wherein the surface (1) for the artificial socket insert is provided with a groove (la) for fitting the insert.

3. The glenoid prosthesis baseplate according to claim 2, wherein the fitting surface (2) is provided with a coating promoting bone ingrowth.

4. The glenoid prosthesis baseplate according to claim 2, wherein the fitting surface (2) is provided with a polyethylene coating.

5. The glenoid prosthesis baseplate according to claim 1, wherein an internal thread is formed in the through hole (2f).

* * * * *